United States Patent
Erkkila et al.

(10) Patent No.: US 9,535,505 B2
(45) Date of Patent: Jan. 3, 2017

(54) USER INTERFACE CONTROL IN PORTABLE SYSTEM

(71) Applicant: Polar Electro Oy, Kempele (FI)

(72) Inventors: Mika Erkkila, Oulu (FI); Pertti Puolakanaho, Kiviniemi (FI); Pekka Rytky, Oulu (FR); Matti Sipola, Oulunsalo (FI); Matti Korpela, Oulu (FI); Juha Sorvala, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 488 days.

(21) Appl. No.: 14/075,736

(22) Filed: Nov. 8, 2013

(65) Prior Publication Data
US 2015/0135078 A1    May 14, 2015

(51) Int. Cl.
| G06F 3/00 | (2006.01) |
|---|---|
| G06F 3/048 | (2013.01) |
| G06F 3/033 | (2013.01) |
| G06F 3/16 | (2006.01) |
| G06F 3/01 | (2006.01) |
| G06F 19/00 | (2011.01) |
| G06F 3/0484 | (2013.01) |
| H04W 4/00 | (2009.01) |

(52) U.S. Cl.
CPC ............ *G06F 3/017* (2013.01); *G06F 3/014* (2013.01); *G06F 3/0484* (2013.01); *G06F 3/167* (2013.01); *G06F 19/3406* (2013.01); *H04W 4/008* (2013.01)

(58) Field of Classification Search
None
See application file for complete search history.

(56) References Cited

U.S. PATENT DOCUMENTS

| 6,115,636 A * | 9/2000 | Ryan ................ A61N 1/37223 128/903 |
|---|---|---|
| 7,113,087 B1* | 9/2006 | Casebolt .............. G01V 3/101 340/539.1 |
| 7,789,800 B1* | 9/2010 | Watterson ........... A63B 21/005 482/1 |
| 8,140,339 B2* | 3/2012 | Hernandez-Rebollar ............... G06K 9/00355 382/182 |

(Continued)

FOREIGN PATENT DOCUMENTS

| EP | 2 239 023 A1 | 10/2010 |
|---|---|---|
| WO | 2012/044334 A2 | 4/2012 |

OTHER PUBLICATIONS

Qifan Pu, Siyu Jiang, and Shyamnath Gollakota, Whole-Home Gesture Recognition Using Wireless Signals (Demo), Aug. 12-16, 2013, 2 pages.*

(Continued)

*Primary Examiner* — Yongjia Pan
(74) *Attorney, Agent, or Firm* — Hoffmann & Baron, LLP

(57) ABSTRACT

This document discloses a portable system comprising a physical activity monitoring device comprising: a wireless proximity detection module configured to detect a proximity of an input control entity with respect to the physical activity monitoring device and output a control signal as a response to the detection, wherein the proximity is a non-zero distance between the input control entity and the training computer; and a user interface controller configured to generate, as a response to the control signal from the wireless proximity detection module, at least one of an audio control function and a display control function.

14 Claims, 5 Drawing Sheets

(56) References Cited

U.S. PATENT DOCUMENTS

| | | | | |
|---|---|---|---|---|
| 8,152,695 B2* | 4/2012 | Riley | ............... | A63B 24/0006 |
| | | | | 482/1 |
| 8,562,487 B2* | 10/2013 | Berggren | ............. | A43B 1/0054 |
| | | | | 482/1 |
| 8,610,582 B2* | 12/2013 | Jeon | ...................... | A63B 71/06 |
| | | | | 340/5.32 |
| 8,764,651 B2* | 7/2014 | Tran | .................... | A61B 5/0022 |
| | | | | 600/300 |
| 9,147,343 B2* | 9/2015 | Johnson | ................ | G08C 19/00 |
| 9,191,829 B2* | 11/2015 | Maguire | ................ | H01Q 1/245 |
| 2006/0007124 A1 | 1/2006 | Dehlin | | |
| 2006/0044112 A1* | 3/2006 | Bridgelall | ......... | G06K 17/0022 |
| | | | | 340/10.1 |
| 2006/0224048 A1* | 10/2006 | Devaul | ............... | A61B 5/0024 |
| | | | | 600/300 |
| 2007/0075965 A1 | 4/2007 | Huppi et al. | | |
| 2007/0100666 A1* | 5/2007 | Stivoric | ............ | G01R 29/0814 |
| | | | | 705/3 |
| 2007/0219059 A1* | 9/2007 | Schwartz | ............ | A61B 5/0205 |
| | | | | 482/8 |
| 2008/0139975 A1* | 6/2008 | Einav | ................... | A61H 1/0262 |
| | | | | 601/33 |
| 2009/0153369 A1* | 6/2009 | Baier | ..................... | G06F 3/014 |
| | | | | 341/20 |
| 2010/0160115 A1* | 6/2010 | Morris | ............... | A63B 22/0235 |
| | | | | 482/4 |
| 2011/0105854 A1 | 5/2011 | Kiani et al. | | |
| 2011/0154258 A1* | 6/2011 | Hope | ................... | H04L 67/125 |
| | | | | 715/810 |
| 2013/0024018 A1* | 1/2013 | Chang | ................... | G08C 17/02 |
| | | | | 700/94 |
| 2013/0169420 A1* | 7/2013 | Blount, Jr. | ............. | G06F 3/014 |
| | | | | 340/12.5 |
| 2013/0271342 A1* | 10/2013 | Shen | .................... | H04B 1/0458 |
| | | | | 343/861 |
| 2013/0324036 A1* | 12/2013 | Hillan | .................. | H04W 8/005 |
| | | | | 455/41.1 |
| 2014/0240214 A1* | 8/2014 | Liu | ........................ | G06F 3/039 |
| | | | | 345/156 |
| 2014/0267148 A1* | 9/2014 | Luna | .................... | G06F 1/3231 |
| | | | | 345/174 |
| 2014/0280156 A1* | 9/2014 | Maser | ................. | G11B 27/031 |
| | | | | 707/737 |
| 2015/0082408 A1* | 3/2015 | Yeh | ...................... | A61B 5/4815 |
| | | | | 726/9 |

OTHER PUBLICATIONS

Michelle Ma, Wi-Fi signals enable gesture recognition throughout entire home, Jun. 4, 2013, 11 pages.*

Qifan Pu, Sidhant Gupta, Shyamnath Gollakota, Shwetak Patel, Whole-Home Gesture Recognition Using Wireless Signals, Sep. 30 to Oct. 4, 2013, 12 pages.*

Anonymous, "Wired Glove", Wikipedia, 3 pages, Sep. 27, 2013.

European Search Report, EP 14191396, 3 pages, Jun. 3, 2015.

* cited by examiner

USER INTERFACE CONTROL IN PORTABLE SYSTEM

BACKGROUND

The invention relates to electronic devices and, in particular, to a controlling a user interface in a portable system.

DESCRIPTION OF THE RELATED ART

Wrist devices such as electronic training computers or, in general, electronic wrist computers comprise a user interface. The user interface is typically limited by the small size of a display and input devices. Therefore, it is beneficial to consider novel technologies to improve the user experience associated with usage of wrist devices.

SUMMARY

According to an aspect, there is provided a portable system comprising a physical activity monitoring device comprising: a wireless proximity detection module configured to detect a proximity of an input control entity with respect to the physical activity monitoring device and output a control signal as a response to the detection, wherein the proximity is a non-zero distance between the input control entity and the training computer; and a user interface controller configured to generate, as a response to the control signal from the wireless proximity detection module, at least one of an audio control function and a display control function.

BRIEF DESCRIPTION OF THE DRAWINGS

In the following the invention will be described in greater detail by means of preferred embodiments with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
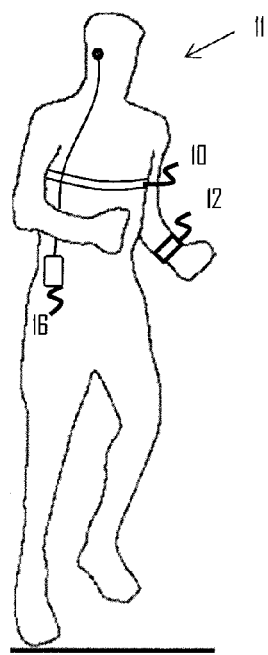
FIGS. 1 and 2 illustrate a portable system to which embodiments of the invention may be applied.
Figure 2:
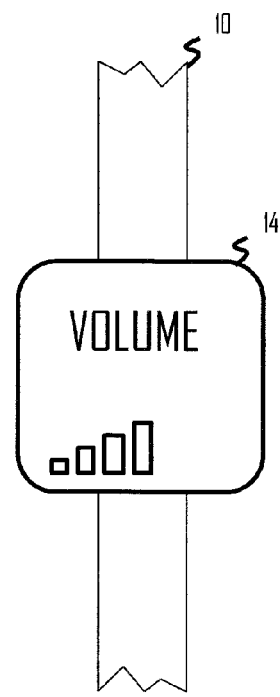

FIGS. 1 and 2 illustrate a system to which some embodiments of the invention may be applied. The system may be a portable system carried by a user 11. The system may comprise a physical activity monitoring device 12, 16 comprising a user interface. The physical activity monitoring device may be a wearable physical activity monitoring device such as a wrist device 12 or a portable physical activity monitoring device such as the wrist device 12, a pocket device 16, a palm device, or a mobile phone. The physical activity monitoring device may be a user interface device. The physical activity monitoring device may be dedicated to the physical activity monitoring or it may be a general purpose device (e.g. the mobile phone) configured to operate as the physical activity monitoring device by a specific computer program application executed in the general purpose device. Under the control of the computer program application, the general purpose device may monitor a physical exercise by receiving and processing measurement data and/or control the physical exercise by outputting instructions to the user via the user interface.

The user interface may comprise an audio interface comprising a loudspeaker and/or an earpiece speaker. The user interface may comprise a visual interface comprising a display screen 14. The physical activity monitoring device 12, 16 may comprise an audiovisual interface comprising both the audio interface and the visual interface. The physical activity monitoring device 12, 16 may comprise an audio playback module configured to play audio tracks stored in a memory of the physical activity monitoring device 12, 16.

The system may further comprise at least one sensor device 10 configured to measure training measurement data. The sensor device 10 may comprise at least one of the following: heart activity sensor, a motion sensor, a force sensor, a cadence sensor, and a location tracking sensor.

Figure 3:
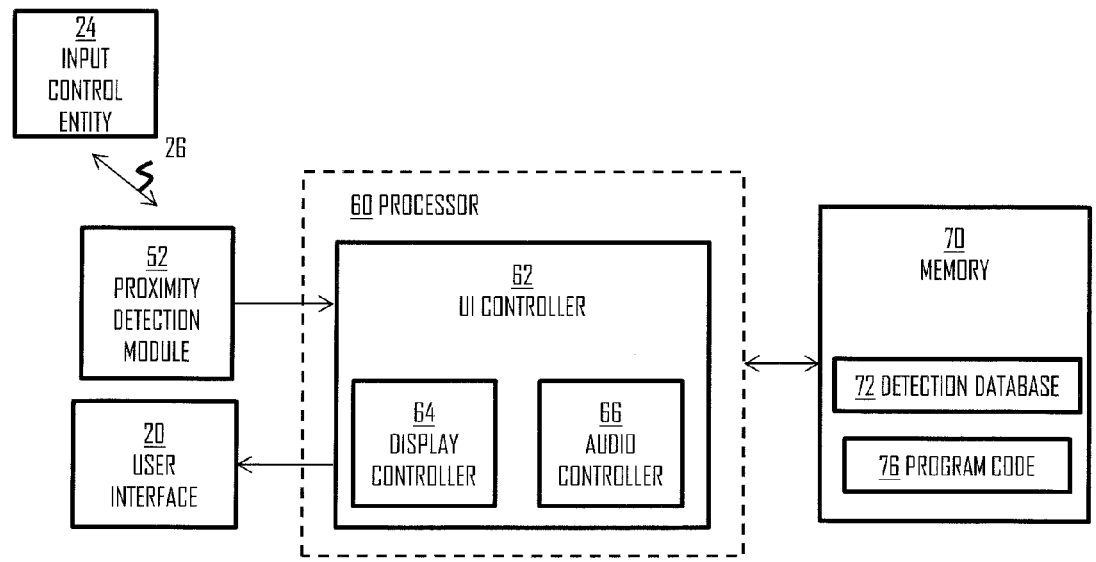
FIG. 3 illustrates a block diagram of a structure of an apparatus according to an embodiment of the invention.

FIG. 3 illustrates a block diagram of a structure of the physical activity monitoring device according to an embodiment of the invention. Referring to FIG. 3, the physical activity monitoring device comprises a wireless proximity detection module 52 configured to detect a proximity of an input control entity 24 with respect to the physical activity monitoring device and output a control signal as a response to the detection. The proximity may be defined as a non-zero distance between the input control entity 24 and the physical activity monitoring device or a sensing element of the proximity detection module 52. The proximity may be defined as a contactless proximity between the input control entity 24 and the physical activity monitoring device or a sensing element of the proximity detection module 52.

The physical activity monitoring device may further comprise at least one processor 60 and at least one memory 70 storing a computer program code 76. The computer program code may comprise program instructions configuring the at least one processor 60 to carry out at least one computer process. In an embodiment, the computer process comprises controlling audio output or visual output according to a control signal received from the proximity detection module 52. In an embodiment, the at least one processor 60 comprises a user interface controller 62 configured to generate, as a response to the control signal from the proximity detection module 52, at least one of an audio control function and a display control function.

The audio control function and/or the display control function may control output of a user interface 20 of the physical activity monitoring device or a user interface with which the physical activity monitoring device communicates over a wireless or a wired connection. In an embodiment where the physical activity monitoring device is the wrist device 12 and the user 11 additionally uses a user interface apparatus 16 such as a portable media player apparatus, the wrist device 12 may control audio and/or display output of the user interface apparatus 16 as a response to the control signal from the proximity detection module 52. The user interface controller 62 may comprise a display controller 64 configured to execute the display control function and/or an audio controller 66 configured to execute the audio control function.

The memory 70 may further store a detection database 72 storing mapping information linking the detected proximity to the audio control function and/or display control function. In an embodiment where the proximity detection module 52 utilizes the detection database 72, the detection database 72 may comprise mapping information mapping the detected proximities to control signals, and the proximity detection module may measure the proximity of the input control entity 24 and map the measured proximity to a corresponding control signal according to the mapping information retrieved from the database 72. In another embodiment where the user interface controller utilizes the detection database 72, the detection database 72 may comprise mapping information mapping the control signals and the control functions of the user interface controller 62. The user interface controller may then receive the control signal from the proximity detection module 52, link the received control signal to an audio control function and/or the display control function according to the mapping information, and instruct the display controller 64 and/or the audio controller 66 to perform a function associated with the received control signal.

Figure 4:
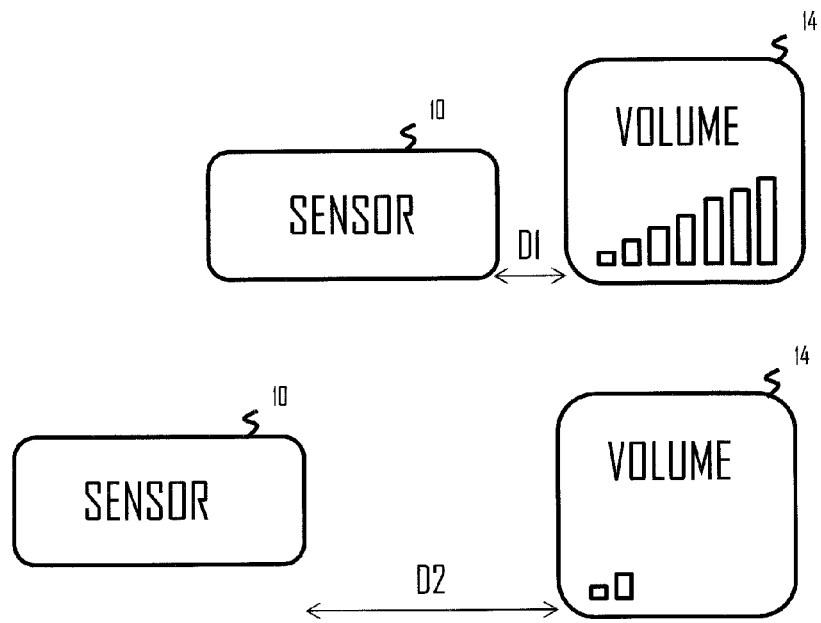
FIGS. 4 and 5 illustrate an embodiment where distance between a sensor device and a physical activity monitoring device is linked to an audio control function and/or a display control function.
Figure 5:
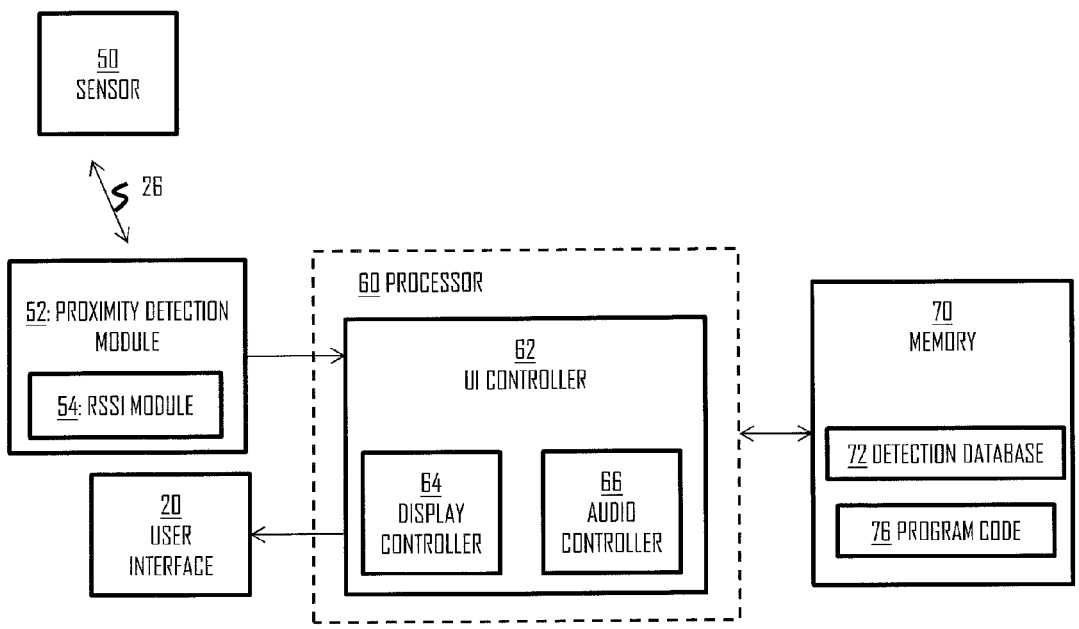

FIGS. 4 and 5 illustrate an embodiment where the input control entity 24 is a sensor device 50, e.g. any one of the above-described sensor devices. The sensor device 50 may be configured to communicate wirelessly with the training computer. The proximity detection module 52 may be configured to measure a signal strength of a wireless signal received from the sensor device 50 and output the control signal according to the measured signal strength. The proximity detection module 52 may comprise a signal strength measuring module 54 configured to measure a received signal strength indicator (RSSI) indicating the signal strength of the signal received from the sensor device 50. The signal strength measuring module 54 may output the measured signal strength as the control signal or use the detection database 72 to map the signal strength to a computer instruction output to the user interface controller 62. The user interface controller 62 may be configured to dynamically adjust at least one of an audio parameter and a display parameter according to the measured signal strength. The user interface controller may map the received control signal to the audio control function and/or the display control function and to adjust at least one of the audio parameter and the display parameter in the corresponding control function according to the contents of the received control signal.

FIG. 4 illustrates an embodiment for dynamically adjusting the audio parameter, e.g. audio volume, according to the measured signal strength. The signal strength estimation in the proximity detection module 52 may be substantially continuous in the sense that the adjustment may be carried out in a linear, stepless, and/or sliding manner. Referring to FIG. 4, a shorter distance D1 between the sensor device 50 and the physical activity monitoring device may be associated to a higher audio volume than a longer distance D2. Accordingly, when the user 11 decreases the distance between the sensor device 50 and the training computer, the user interface controller is configured to raise the audio volume. Similarly, when the user 11 increases the distance between the sensor device 50 and the training computer, the user interface controller 62 is configured to decrease the audio volume. This enables the user 11 to execute the adjustment of the audio parameter and/or the display parameter by altering the distance between the sensor device 50 and the training computer. For example, when the sensor device 50 is the heart activity sensor attached to the user's 11 chest, the user may increase the audio volume by bringing the physical activity monitoring device closer to the chest. The user 11 may first activate the adjustment of the audio parameter or the display parameter in the physical activity monitoring device and, after the activation, the proximity detection module 54 starts the measurements. Thereafter, the user 11 may carry out the adjustment by altering the distance between the sensor device 50 and the training computer.

It should be appreciated that the shorter distance may be associated to a lower audio volume and the longer distance to a higher audio volume in the embodiment of FIG. 4.

In some embodiments, a communication interval between the sensor device 50 and the physical activity monitoring device is long, e.g. one message in one second intervals. Accordingly, the distance may be measured with substantially low periodicity. In an embodiment of FIG. 4, the physical activity monitoring device is configured to output a notification at the timing when the measurement is made. The notification may comprise an audio signal and/or vibration. Accordingly, the user may adopt the change of the distance to the measurement periodicity. Upon triggering the distance measurements, the first distance measurement may be configured as a reference point and it may be associated with the current state of the audio/display control function, e.g. audio volume. A first notification may be output as an indication that the reference point has been measured. Then, the user may change the distance between the sensor device and the physical activity monitoring device. During the next communication, the distance measurement is made once again, and the user is notified with a second notification, wherein the second notification may be different from the first notification, e.g. an audio output of increased or decreased audio frequency. A second, third or, subsequent distance measurement may then serve as a final distance measurement and the degree of adjustment of the audio/display control function may be determined on the basis of the difference between the first distance measurement and the final distance measurement. A final notification may then also be output to the user, wherein the final notification may differ from the previous notifications and, thus, indicate that the adjustment is made.

In other embodiments where the communication interval is shorter, e.g. less than 0.5 seconds, less than 0.3 seconds, or less than 0.1 seconds, the notifications at the measurement timings is necessarily not needed. For example, the embodiment of FIG. 4 may be realized in a scenario where the distance is measured between two physical activity monitoring devices, e.g. a wrist computer and a mobile phone. Communication between such devices may employ shorter communication intervals.

In an embodiment of FIG. 4, the activation of the adjustment of the audio/display control function is carried out by bringing the physical activity monitoring device and the sensor device into each other's close proximity. In this embodiment, the activation of the adjustment of the audio/ display control function may be triggered upon measuring an RSSI exceeding a determined activation threshold. In an embodiment, the activation of the audio/display control function may cause at least one of the physical activity monitoring device and the sensor device to shorten the communication interval in order to carry out the distance measurements with a higher measurement frequency. Upon completing the distance measurements, the original communication interval may be resumed. A similar dynamic adjustment may be realized by equipping the physical activity monitoring device with an inertial sensor for sensing inertial forces subjected to the training computer, wherein the user interface controller 62 is further configured to generate the at least one of the audio control function and the display control function based on the forces sensed by the inertial sensor. The memory 70 may store a motion reference database configured to store reference motion trajectories of the training computer, each reference motion trajectory mapped to at least one audio control function or at least one display control function, wherein the inertial sensor is configured to measure a motion trajectory from the inertial forces subjected to the training computer. The physical activity monitoring device may further comprise a comparator configured to compare the measured motion trajectory with at least one reference motion trajectory and determine a reference motion trajectory providing the best match with the measured motion trajectory and output a control signal corresponding to the determined reference motion trajectory to the user interface controller. The user interface controller may be configured to generate at least one of the audio control function and the display control function mapped to the determined reference motion trajectory. In an embodiment, the detected proximity of the input control entity 24 may cause the physical activity monitoring device to activate the inertial sensor to start the measurements.

In an embodiment, the audio control function comprises at least one of the following: adjusting an audio volume; changing an audio track, starting an audio track, stopping an audio track, pausing an audio track, recording an audio track, outputting an exercise guidance audio signal; selecting a sound profile, and selecting a playback device.

In an embodiment, the display control function comprises at least one of the following: switching from an audio player display mode to an exercise display mode, changing brightness of a display light, zooming a display view in/out, changing one exercise display mode to another exercise display mode, accepting an incoming call, and dismissing the incoming call. With respect to said accepting the incoming call, the display control function may comprise switching a display mode from notification of pending incoming call to a display mode indicating that the call is connected and voice connection is on. With respect to said accepting the incoming call, the display control function may comprise switching a display mode from notification of pending incoming call to a display mode indicating that the incoming call has been dismissed.

The zooming and the change of the audio volume and the brightness are substantially linear so they may be adjusted by using the embodiment of FIG. 4. Furthermore, the selection of the next or previous track may be carried out by using the embodiment of FIGS. 4 and 5. For example, when the physical activity monitoring device is in a mode in which it receives instructions for changing the track, the proximity detection module may estimate the changes in the distance between the physical activity monitoring device and the sensor device 50 by measuring the signal strength. The mode may be triggered by receiving a user input, for example, and the distance at the time of triggering the mode may be used as a reference for determining the change of the distance. Upon detecting that the distance decreases, it may output a control signal controlling the user interface controller to select the next track. Upon detecting that the distance increases, the proximity detection module 52 may output a control signal controlling the user interface controller to select the previous track. In another embodiment, the decreasing distance causes the selection of the previous track, and the increasing distance causes the selection of the next track. The accepting/dismissing the call may be carried out in substantially similar manner: detection of the increasing distance may trigger one of the dismissal/acceptance and detection of the decreasing distance may trigger the other of the dismissal/acceptance.

Figure 6:
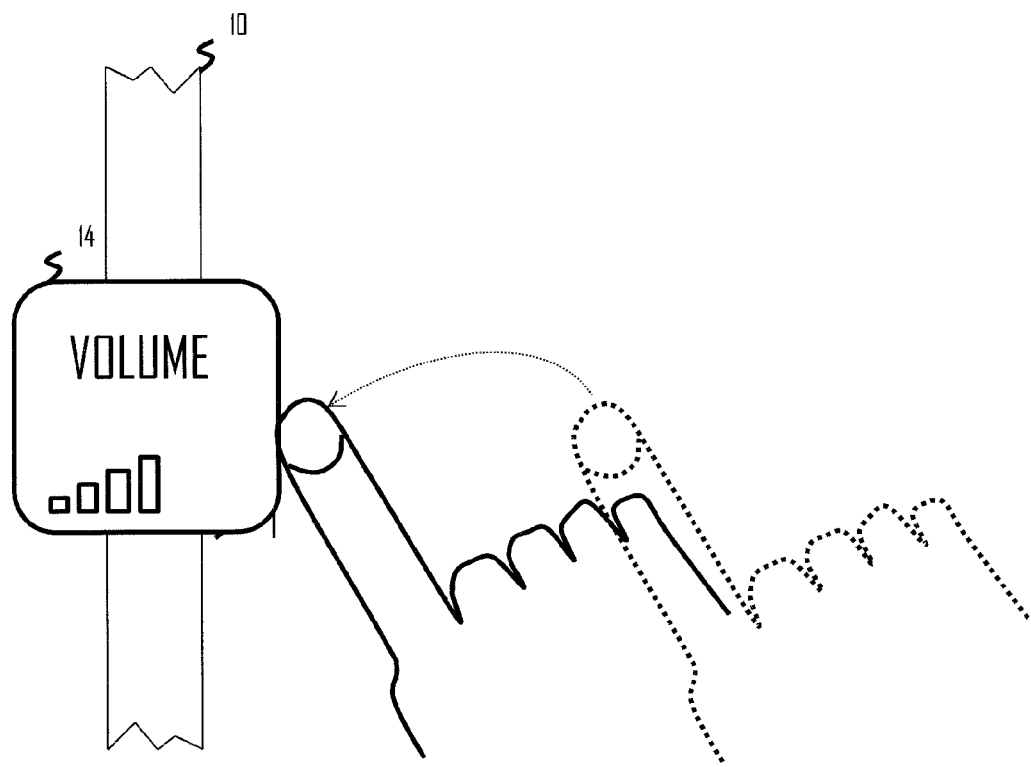
FIGS. 6 and 7 illustrate an embodiment of wireless sensing of proximity of a user's hand with respect to the physical activity monitoring device and linking the sensed proximity to the audio control function and/or display control function.
Figure 7:
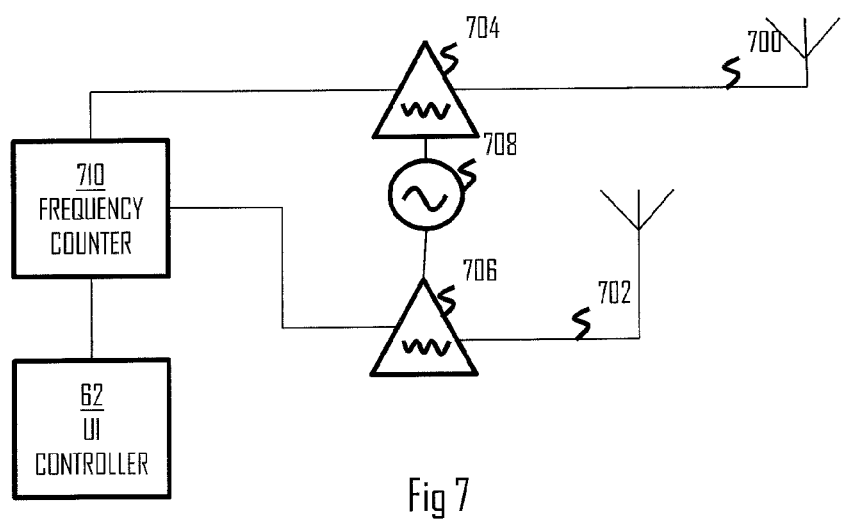

In an embodiment, the input control entity is a human hand, a part of a human hand such as a finger, or another pointer causing changes in an electric field around the proximity detection module when the input control entity is moved with respect to the proximity detection module. FIGS. 6 and 7 illustrate this embodiment. The proximity detection module 52 may comprise at least one antenna 700, 702 and an antenna impedance monitoring circuitry configured to monitor a change in antenna impedance caused by moving the input control entity with respect to the at least one antenna and to output the control signal according to the monitored antenna impedance.

In the embodiment of FIG. 7, the proximity detection module 52 comprises at least two orthogonally disposed antennas 700, 702. The antennas 700, 702 may be disposed orthogonally with respect to each other such that they sense orthogonal components of an electromagnetic field around the proximity detection module 72. The antennas 700, 702 may each sense electromagnetic radiation along one axis, and the third dimension of the electromagnetic field may be estimated by processing the radiation sensed by two antennas 700, 702 separated sufficiently from each other. In particular, the antennas 700, 702 may be configured to sense proximity and degree of proximity in a direction that is orthogonal to a plane formed by mechanics of the training computer, e.g. a plane formed by a circuit board of the training computer.

In an embodiment, the antennas are micro-strip antennas integrated into a circuit board.

In an embodiment, the proximity detection module 52 further comprises an impedance conversion circuitry configured to convert a detected change in the sensed electromagnetic field into said control signal output to the user interface controller 62. In the embodiment of FIG. 7, the impedance conversion circuitry comprises an oscillator 708 connected to an input of a resonance circuitry 704, 706 configured to provide a resonance frequency as a function of a control signal received from the respective antenna 700, 702. Each resonance circuitry 704, 706 may have its other input connected to a respective antenna 700, 702. Referring to FIGS. 6 and 7, when the user 11 moves his hand or finger within the proximity of the training computer, the electromagnetic field sensed by the antennas 700, 702 changes, the impedance of the antennas 700, 702 changes as well, and the antennas apply a changed signal to the resonance circuitries 704, 706. As a response, the resonance frequency of the resonance circuitries 704, 706 changes and they output a changed resonance signal to a frequency counter module 710. The frequency counter 710 may be configured to map the detected resonance frequencies of the resonance circuitries 710 to a determined control signal and output the control signal to the user interface controller. As a response to the received control signal, the user interface controller 62 may execute the audio control function and/or the display control function. The detection database 72 may store the mappings between the resonance frequencies or resonance frequency combinations and corresponding control signals. The resonance frequencies or resonance frequency combinations stored in the detection database 72 may represent static position of the input control entity with respect to the antenna(s) 700, 702 or motion of the input control entity with respect to the antenna(s) 700, 702. Accordingly, a single resonance frequency, a single resonance frequency per antenna, or a sequence of resonance frequencies per antenna may be mapped to each control signal.

Figure 8:
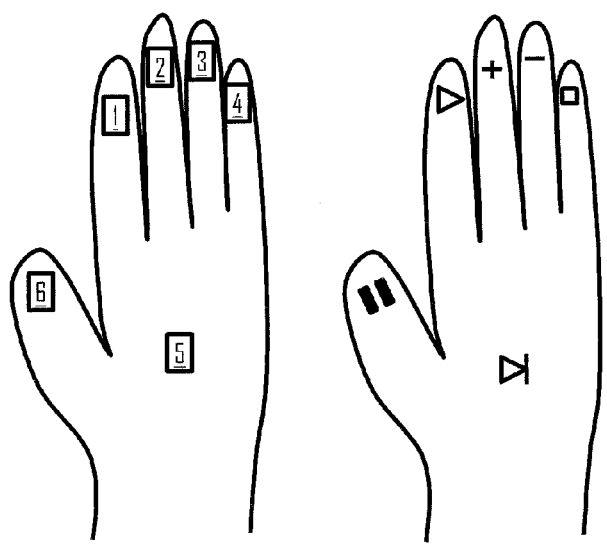
FIGS. 8 and 9 illustrate an embodiment where a user interaction device controls the audio control function and/or display control function of the training computer.

With the embodiment of FIGS. 7 and 8, it is possible to provide a wireless switch or a wireless button, wherein the user may operate the switch by bringing his/her hand close to the physical activity monitoring device or moving the hand with respect to the training computer. The detection of the electromagnetic field corresponding to the scenario where the user's 11 hand is within the proximity of the antennas 700, 702 may activate a determined function in the training computer. The function may be a selection function. The detection of an electromagnetic field corresponding to the scenario where the user's 11 hand is moved linearly within the proximity of the antennas may activate a determined adjustment function, e.g. a sliding adjustment of a volume or zoom function. The linear movement of the hand may be directed towards or away from the physical activity monitoring device to realize a different sliding function. Different motions of the hand within the proximity of the antennas may trigger different functions in the physical activity monitoring device according to the changes in the electromagnetic field sensed by the antennas and the impedance conversion circuitry.

In an embodiment, the proximity detection module 52 may activate the impedance conversion circuitry upon receiving an activation signal through a user interface of the training computer, e.g. user operation of a physical button or selection of a determined operating mode. As response to the activation, the impedance conversion circuitry may start the sensing of the gestures from the impedance of the antennas 700, 702. The impedance conversion circuitry may be deactivated upon receiving a deactivation signal through the user interface and/or upon detecting from the antenna impedance(s) that the hand is no longer within the proximity of the antennas.

In another embodiment, the impedance conversion circuitry may operate autonomously and start the sensing of the gestures upon detecting the proximity of the hand with respect to the antennas.

In an embodiment, the input control entity comprises an interaction device configured to communicate wirelessly with the training computer.

The proximity detection module 52 may comprise an energizing circuitry 92 configured to wirelessly energize the interaction device, read data from the interaction device as a result of the energization, and output the control signal as a response to the read data. The data read from the interaction device may comprise a device address of the interaction device, and the user interface controller 62 may be configured to modify the at least one of the audio control function and the display control function according to the device address. Accordingly, the detection database 72 may provide mapping between different device addresses and corresponding control functions.

Figure 9:
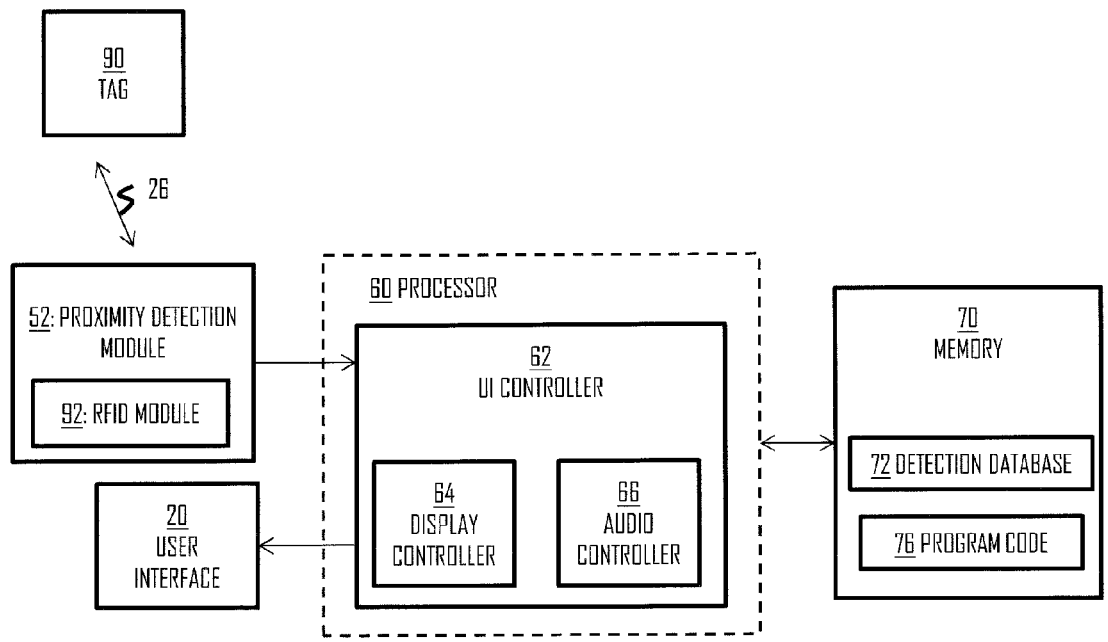

Referring to FIGS. 8 and 9, the interaction device may comprise at least one of a radio frequency identification (RFID) tag 90 and a near-field communication tag 90. The tag may be passive in the sense that it does not need any battery and acquires the necessary electric power from the energization caused by an RFID module of the proximity detection module 52.

In an embodiment, the interaction device comprises an apparel comprising the at least one tag 1, 2, 3, 4, 5, 6. The tag may be sewn into the apparel and a marking indicating a function associated with each tag may be disposed in connection with the tag in the apparel.

With respect to the embodiment of FIGS. 8 and 9, the user 11 may trigger different audio or display control functions by bringing the corresponding tag close to the training computer. The RFID module 92 may send interrogation signals energizing any tags within an interrogation range of the RFID module 92 and, upon bringing a tag to the interrogation range, the RFID module is able to read the data from the tag 90 and trigger a corresponding function. The interrogation range may be a few centimeters, e.g. less than one or two centimeters such that false readings are avoided.

FIG. 8 illustrates an embodiment where the apparel comprises a glove comprising at least one of said tags at a first side of a finger portion of the glove and a symbol indicating a function associated of the at least one of said tags at an opposite side of the finger portion. In an embodiment, the first side is the inner side contacting the user's 11 palm and used to grip or point objects. The second side is the opposite side that contacts the back of the hand. The symbol may be provided on the second side at the same location as the location of the corresponding tag on the first side. For example, if a tag comprised on the first side of an index finger portion of the glove is associated with an audio control function "play", the corresponding "play" symbol may be disposed on the second side of the index finger portion of the glove. The tags may be provided in one or both of the left hand glove and the right hand glove.

In the embodiment where the apparel is the glove, the user 11 may trigger the selected audio or display control function by bringing the finger or any other portion of the glove where the tag is disposed within the proximity of the training computer. Accordingly, the desired functions may be executed without taking the gloves off of the hand. In an embodiment where the apparel is a coat, a jacket, or trousers, the user 11 may trigger the selected audio or display control function by bringing the physical activity monitoring device close to the portion of the apparel where the tag 90 is disposed.

In an embodiment, the physical activity monitoring device is configured to establish a wireless connection with an external media player, and wherein the user interface controller is configured to send a signal of the audio control function and/or the display control function to the external audio player through the wireless connection. For example, the wrist device 12 may control the audio or display output of the portable media player 16.

In another embodiment, the physical activity monitoring device further comprises an integrated audio device and/or display, and wherein the user interface controller is configured to control the integrated audio device with the audio control function and the display with the display control function.

Figure 10:
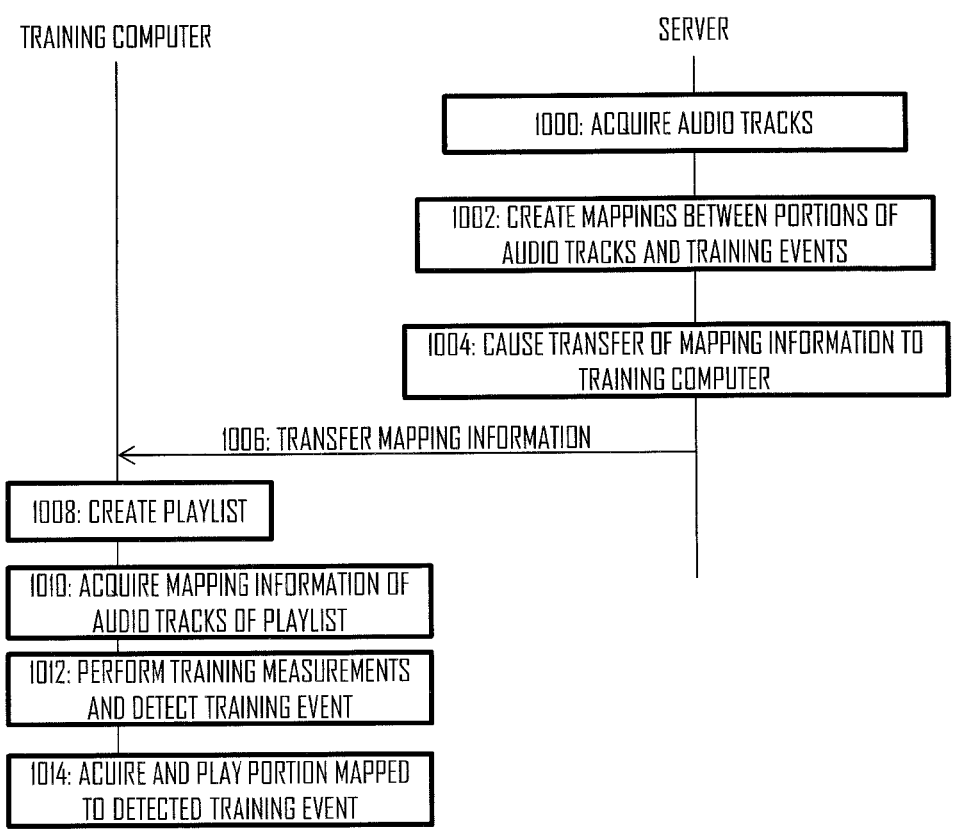
FIG. 10 illustrates a diagram of an embodiment for mapping portions of audio tracks with training events.

FIG. 10 illustrates a diagram of yet another embodiment. FIG. 10 illustrates an embodiment where an audio track or a portion of the audio track is mapped to a training event of a physical exercise. The physical activity monitoring device may monitor the physical exercise of the user 11 by analyzing measurement data measured by at least one sensor device 50. Upon detecting the training event on the basis of the analysis, the processor 60 may cause the user interface controller 62 to play the audio track mapped to the detected training event. Some steps of FIG. 10 may be carried out in the training computer, while other steps may be carried out in a computer apparatus such as a network server computer. The computer apparatus may comprise at least one processor and at least one memory storing a computer program code of program instructions causing the at least one processor to execute a computer process. The computer process may comprise at least some of the steps described below with respect to the server computer.

Referring to FIG. 10, the server computer may acquire one or more audio tracks in block 1000. The audio tracks may be comprised in a playlist created by the user 11. In block 1002, the server computer creates mappings between portions of the acquired audio tracks and training events. The portions may be selected on the basis of song lyrics or tempo of the audio track and associated with corresponding training events. Block 1002 may comprise generating a portion of an audio track and storing definitions of the portion in association with an identifier of the training events associated with the portion. The definitions of the portion may comprise an identifier of the audio track and start and end times of the portion. For example, a training event of high training intensity, e.g. a heart rate over 170 beats per minute, may be linked to a high-tempo portion of an audio track or a portion including spurring lyrics.

In block 1004, the processor of the server computer causes transmission of the mapping information created in block 1002 to the training computer. The mapping information is transferred from the server computer to the physical activity monitoring device in step 1006 over one or more wired or wireless connections.

In block 1008, the physical activity monitoring device creates a playlist comprising a plurality of audio tracks. In block 1010, the physical activity monitoring device retrieves the mapping information from a memory, e.g. as a response to playback of the playlist. The physical activity monitoring device may retrieve a portion of the mapping information, e.g. the identifiers of the training events the physical activity monitoring device is configured to detect. In block 102, the physical activity monitoring device analyses training measurement data received from at least one sensor device and scans for the training events. Upon detecting one or more of the training events, the physical activity monitoring device is configured to cause playback of the portion mapped to the detected one or more training events.

The physical activity monitoring device may cause immediate playback of the portion regardless of whether or not an audio track is currently played. In another embodiment, the physical activity monitoring device is configured to cause the playback of the portion when the currently played track ends. Accordingly, the playback of the portions may be scheduled to the next idle time interval between two consecutive audio tracks.

In an embodiment, a further categorization of the portions may be created in block 1002 by mapping the portion to one or more sports types. Accordingly, the portion may be used only when the physical exercise belongs to the sports type mapped to the portion.

In an embodiment, the physical activity monitoring device is configured to select a portion that is already included in the playlist or a portion that is comprised in an audio track of an artist comprised in the playlist.

As used in this application, the term 'circuitry' refers to all of the following: (a) hardware-only circuit implementations such as implementations in only analog and/or digital circuitry; (b) combinations of circuits and software and/or firmware, such as (as applicable): (i) a combination of processor(s) or processor cores; or (ii) portions of processor(s)/software including digital signal processor(s), software, and at least one memory that work together to cause an apparatus to perform specific functions; and (c) circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one core of a multi-core processor, and its (or their) accompanying software and/or firmware. The term "circuitry" would also cover, for example and if applicable to the particular element, a baseband integrated circuit, an application-specific integrated circuit (ASIC), and/or a field-programmable grid array (FPGA) circuit for the apparatus according to an embodiment of the invention.

The processes or methods described above in connection with FIGS. 3 to 10 may also be carried out in the form of a computer process defined by a computer program. The computer program may be in source code form, object code form, or in some intermediate form, and it may be stored in some sort of carrier, which may be any entity or device capable of carrying the program. Such carriers include transitory and/or non-transitory computer media, e.g. a record medium, computer memory, read-only memory, electrical carrier signal, telecommunications signal, and software distribution package. Depending on the processing power needed, the computer program may be executed in a single electronic digital processing unit or it may be distributed amongst a number of processing units.

The present invention is applicable to portable systems defined above but also to other suitable systems. The development of the systems may require extra changes to the described embodiments. Therefore, all words and expressions should be interpreted broadly and they are intended to illustrate, not to restrict, the embodiment. It will be obvious to a person skilled in the art that, as technology advances, the inventive concept can be implemented in various ways. The invention and its embodiments are not limited to the examples described above but may vary within the scope of the claims.

What is claimed is:

1. A portable system comprising:
a wearable physical activity monitoring device comprising a wireless proximity detection module configured to detect a proximity of an input control entity with respect to the physical activity monitoring device and output a control signal as a response to the detection, wherein the proximity is a non-zero distance between the input control entity and the physical activity monitoring device, and wherein the input control entity is a user's hand or a part of the user's hand or an interaction device worn or carried by the user, and the wearable physical activity monitoring device further comprising a user interface controller configured to generate, in response to the control signal received from the wireless proximity detection module, at least one of an audio control function and a display control function, the input control entity being in the form of said interaction device configured to communicate wirelessly with the physical activity monitoring device, the interaction device comprises at least one of a radio frequency identification tag and a near-field communication tag, the interaction device comprises an apparel comprising the at least one of the radio frequency identification tag and the near-field communication tag, the apparel comprises at least one glove comprising at least one of said radio frequency identification tag and near-field communication tag at a first side of a finger portion of the glove and a symbol indicating a function associated with the at least one of said radio frequency identification tag and near-field communication tag at an opposite side of the finger portion.

2. The portable system of claim 1, wherein the proximity detection module comprises an energizing circuitry configured to wirelessly energize the interaction device, read data from the interaction device as a result of the energization, and output the control signal as a response to the read data.

3. The portable system of claim 1, wherein the proximity detection module is configured to acquire a device address of the interaction device; and wherein the user interface controller is configured to modify the at least one of the audio control function and the display control function according to the device address.

4. The portable system of claim 1, wherein the interaction device is a sensor device configured to communicate wirelessly with the physical activity monitoring device, wherein the proximity detection module is configured to measure a signal strength of a wireless signal received from the sensor device, and wherein the user interface controller is configured to dynamically adjust a display parameter according to the measured signal strength.

5. The portable system of claim 4, wherein the proximity detection module is configured to cause the sensor device to shorten a communication interval in response to triggering the signal strength measurement.

6. The portable system of claim 1, wherein the physical activity monitoring device further comprises an inertial sensor for sensing inertial forces subjected to the physical activity monitoring device, and wherein the user interface controller is further configured to generate the at least one of the audio control function and the display control function based on the detected proximity of the input control entity and the inertial forces sensed by the inertial sensor.

7. The portable system of claim 6, further comprising:

a motion reference database configured to store reference motion trajectories of the training computer, each reference motion trajectory mapped to at least one audio control function or at least one display control function, wherein the inertial sensor is configured to measure a motion trajectory from the inertial forces subjected to the training computer;

a comparator configured to compare the measured motion trajectory with at least one reference motion trajectory and determine a reference motion trajectory providing the best match with the measured motion trajectory, the user interface controller being configured to generate at least one of an audio control function and a display control function mapped to the determined reference motion trajectory.

8. The portable system of claim 1, wherein the input control entity is said user's hand or said part of the user's hand, and wherein the proximity detection module comprises at least one antenna and an antenna impedance monitoring circuitry configured to monitor a change in an antenna impedance caused by moving the input control entity with respect to the at least one antenna and output the control signal according to the monitored antenna impedance.

9. The portable system of claim 8, wherein the proximity detection module comprises at least two orthogonally disposed antennas.

10. The portable system of claim 1, wherein the at least one of the audio control action and the display control function is selected from the group comprising: changing an audio track, stopping an audio track, pausing an audio track, recording an audio track, outputting an exercise guidance audio signal; selecting a sound profile, and selecting a playback device, and wherein the display control function comprises at least one of the following: switching from an audio player display mode to an exercise display mode, changing brightness of a display light, zooming a display view in or out, changing one exercise display mode to another exercise display mode, accepting an incoming call, and dismissing the incoming call.

11. The portable system of claim 1, wherein the physical activity monitoring device is configured to establish a wireless connection with an external audio player, and wherein the user interface controller is configured to send the audio control function to the external audio player through the wireless connection.

12. The portable system of claim 1, wherein the physical activity monitoring device further comprises an integrated audio device, and wherein the user interface controller is configured to control the integrated audio device with the audio control function.

13. The portable system of claim 1, wherein the physical activity monitoring device is a wrist computer.

14. The portable system of claim 1, wherein the wearable physical activity monitoring device further comprises a detection database storing mapping information linking different proximities of the input control entity to different control signals, and wherein the wireless proximity detection module is further configured to measure a proximity of the input control entity with respect to the physical activity monitoring device, map the measured proximity to a corresponding control signal according to the mapping information retrieved from the detection database, and to output the corresponding control signal to the user interface controller.

* * * * *